United States Patent
He et al.

(10) Patent No.: US 7,524,640 B2
(45) Date of Patent: Apr. 28, 2009

(54) INHIBITING SMAD2/3 SIGNALING PROMOTES NEURITE OUTGROWTH IN DORSAL ROOT GANGLIA

(75) Inventors: Zhigang He, Boston, MA (US); Fan Wang, Durham, NC (US)

(73) Assignees: Children's Medical Center Corporation, Boston, MA (US); Duke University, Durham, NC (US)

( * ) Notice: Subject to any disclaimer, the term of this patent is extended or adjusted under 35 U.S.C. 154(b) by 0 days.

(21) Appl. No.: 11/499,055

(22) Filed: Aug. 6, 2006

(65) Prior Publication Data

US 2008/0031911 A1 Feb. 7, 2008

(51) Int. Cl.
*G01N 33/567* (2006.01)
*C12N 5/06* (2006.01)
*C12N 5/00* (2006.01)
*C12N 5/08* (2006.01)
*C12N 5/16* (2006.01)
*A01N 1/00* (2006.01)

(52) U.S. Cl. ............... 435/7.21; 435/368; 435/326; 435/366; 435/1.1

(58) Field of Classification Search ............... None
See application file for complete search history.

(56) References Cited

OTHER PUBLICATIONS

Blight Nat. Neurosci. 2002. 5: 1051-4.*
Schmidt et al. Annu. Rev. Biomed. Eng. 2003. 5: 293-347.*
Hoke et al. Nat. Clin. Pract. Neurol. 2006: 448-454.*
't Hart et al. Curr. Opin. Neurol. 2003. 16: 375-383.*
Nash et al. J. Neurosci. Aug. 15, 2002. 22: 7111-7120.*

* cited by examiner

*Primary Examiner*—Christine J Saoud
*Assistant Examiner*—Chang-Yu Wang
(74) *Attorney, Agent, or Firm*—Richard Aron Osman

(57) ABSTRACT

Regeneration of a lesioned CNS axon of a mature neuron, determined to be subject to regeneration inhibition by Smad2/3 signaling, is promoted by contacting the neuron with an inhibitor of Smad2/3 signaling sufficient to promote regeneration of the axon.

1 Claim, No Drawings

INHIBITING SMAD2/3 SIGNALING PROMOTES NEURITE OUTGROWTH IN DORSAL ROOT GANGLIA

This work was supported by NIH Grant Nos. NIDCR 5RO1 DE16550 and NINDS 1R01NS051788 The U.S. government may have rights in any patent issuing on this application.

BACKGROUND OF THE INVENTION

The field of the invention is inhibition of Smad2/3 signaling to promote regeneration of a lesioned CNS axon of a mature neuron.

The regeneration failure following injury to the adult mammalian CNS has been attributed to both the inhibitory extrinsic environment of the adult CNS, as well as the diminished intrinsic ability of mature axons to regenerate. Recent progress in examining the molecular mechanisms of inhibitory molecules associated with both CNS myelin and the glial scar has led to the development of various genetic and pharmacological means to block these inhibitory activities (Filbin, 2003; Harel and Strittmatter, 2006; Yiu and He, 2006; Schwab and Bartholdi, 1996; Silver and Miller, 2004). When applied to different in vivo injury models, however, these treatments have resulted in limited to no regeneration of lesioned axons (Case and Tessier-Lavigne, 2005; Thuret et al., 2006, Yiu and He, 2006). While it is possible that more comprehensive combinatorial treatments may further enhance the extent of axonal regeneration, a more likely possibility is that strategies that only target inhibitory signals are not sufficient to promote a significant level of regeneration. In fact, even a permissive environment, such as a sciatic nerve graft transplanted to the lesion site, only allows a small percentage of injured adult axons to regenerate into the graft (Aguayo et al., 1990; Schwab and Bartholdi, 1996). These results indicate that other mechanisms, such as those controlling the intrinsic axonal growth potential of neurons, may play important roles in axon regeneration.

Primary sensory neurons with cell bodies in trigeminal and dorsal root ganglia (DRG) have often been used as a model to study the mechanisms controlling the intrinsic growth ability of axons. These neurons possess two major branches stemming from a unipolar axon: a peripheral axon that innervates peripheral targets such as skin, viscera, and muscles, and a central axon that relays the information to the spinal cord or brain stem. In the adult, the peripheral and central branches differ dramatically with regard to their ability to regenerate after axotomy. While peripheral axons can readily regrow after lesioning, the injured central branch from the same DRG neuron may only sprout abortively but cannot regenerate. Interestingly, a conditioning lesion first made in the peripheral branch can dramatically increase the ability of the central axons to regenerate in the dorsal columns (Richardson and Issa, 1984; Richardson and Verge, 1986; Chong et al., 1996; Oudega et al., 1994; Neumann and Woolf, 1999; Neumann et al., 2005). In other words, the exuberant sprouting pattern of naive DRG neurons can be converted to efficient regenerative elongation by a priming peripheral nerve lesion (known as a "preconditioning lesion"). Importantly, these different regenerative competence states (before and after pre-conditioning lesion) can also be recapitulated in vitro. During the first day in culture, naive adult DRG neurons usually elaborate an "arborizing" growth pattern with compact, highly-branched arbors, while pre-conditioned cells exhibit an "elongating" phenotype with rapid extension of long, sparsely-branched axons (Smith and Skene, 1997; Bomze et al., 2001; Lankford et al., 1998; Liu and Snider, 2001; Neumann et al., 2005; Neumann and Woolf, 1999;). However, the molecular mechanism that triggers the loss of regenerative ability in mature neurons and how that may be reversed in pre-conditioned neurons remain unclear.

A possible clue to understanding the mechanisms controlling the regenerative ability of axons can be traced to the establishment of axonal connections during development. In general, when axons reach their targets, the motile growth cones of the developing axons progressively cease growing and transform over time into mature synaptic terminals with new functions and a distinct set of proteins (Hall and Sanes, 1993). For most neurons, this transformation involves the decreased expression of growth cone components (Basi et al., 1987; Caroni and Becker, 1992; Chu and Klymkowsky, 1989; Hoffman, 1989; Maness et al., 1988; Miller et al., 1989; Skene et al., 1986). It is conceivable then that the signals derived from presynaptic terminals and/or postsynaptic targets may instruct the neuronal somas to reprogram their growth states, thus leading to the loss of axonal regenerative ability in mature neurons. In this respect, it has been shown that a contact-dependent signal from amacrine cells innervating neonatal retinal ganglion neurons could trigger a loss of axonal growth ability (Goldberg et al., 2002). However, it remains unknown whether this mechanism may also apply to other types of neurons, and the identity of the molecular signal(s) that switch off the intrinsic regenerative capacity remains elusive.

In sensory neurons from DRGs, the time when axons reach their respective targets differs in different sub-groups. Cutaneous afferents appear in rat proximal hindlimb on embryonic days 14-15 (E14-15) and in the skin of toes at E16-17 (Mimics and Koerber, 1995a; Mimics and Koerber, 1995b). These fibers are functional soon afterwards, beginning at E18-19 (Fitzgerald, 1991; Saito, 1979). This is temporally correlated with the expression of different neurotransmitters such as calcitonin gene related peptide (CGRP) in DRG neurons innervating skin and viscera (Gibson et al., 1984; Hall et al., 1997; Lee et al., 1985a; Lee et al., 1985b), suggesting that target derived factors could act as retrograde signals to alter the program of neuronal differentiation. Interestingly, interruption of retrograde transport in the peripheral axons by transection, ligation, or local application of the microtubule-depolymerizing agent colchicine to the sciatic nerve, can enhance axonal growth ability when these neurons are cultured in vitro (Bomze et al., 2001; Lankford et al., 1998; Neumann and Woolf, 1999; Smith and Skene, 1997), consistent with the idea that signals emanating from peripheral targets also regulate the axonal growth ability of DRG neurons.

Several classes of molecules, such as neurotrophins, Wnts and TGFβ family members, have been implicated in regulating different aspects of neuronal differentiation and function via retrograde transport (reviewed by Ginty and Segal, 2002; Hippenmeyer et al., 2004; Howe and Mobley, 2005; Zweifel et al., 2005). A well-established example is the control of neuronal survival by the presence of limiting amounts of target-derived neurotrophic factors (Bibel and Barde, 2000; Campenot and MacInnis, 2004; Ginty and Segal, 2002; Zweifel et al., 2005). In addition, studies both in cell culture and in vivo have implicated TGFβ family members produced in skin, notably activin A, as inducers of CGRP expression in DRG neurons (Ai et al., 1999; Hall et al., 1997; Hall et al., 2001 McMahon et al., 1989). TGFβ family members, which include activins, TGFβs, and BMPs among others, bind to type I and type II cell surface receptors (Shi and Massague, 2003). A major class of downstream mediators known as the Smad family of signal transducing proteins could then relay the activated signal from the cell membrane of axonal terminals to the nucleus via retrograde transport. In the nucleus, Smads collaborate with other co-activators and repressors to trigger transcriptional responses that are specific for different biological processes (Attisano and Wrana, 2002; Derynck and Zhang, 2003; Massague et al., 2005).

TGFβ members and their receptors are expressed in peripheral targets and sensory neurons not only during development but also in adulthood (Ai et al., 1999; Rogister et al., 1993; Stark et al., 2001). Moon and Fawcett (Eur J Neurosci. (2001) 14:1667-77) report a reduction in CNS scar formation without concomitant increase in axon regeneration following treatment of adult rat brain with a combination of antibodies to TGFβ1 and TGFβ2.

In studies with embryonic Xenopus explants, both truncated activin type II receptor and follistatin (a protein derived from the embryonic Spemann Organizer) block activin signaling and neuralize cells that would otherwise become epidermal cells (Hemmati-Brivanlou et al. Cell (1994) 77:273-281; Cell (1994) 77:283-295). These Hemmati-Brivanlou et al. papers only address differentiation of embryonic cells, and do not mention, discuss, nor have any relevance to differentiated, adult cell types, such as post-mitotic, differentiated adult neurons.

Hemmati-Brivanlou et al. submitted these same data in a patent application (now, U.S. Pat. No. 6,686,198) which they accurately abstract as relating to differentiation of embryonic cells: "The subject method stems from the unexpected finding that, contrary to traditional understanding of neural induction, the default fate of ectodermal tissue is neuronal rather than mesodermal and/or epidermal. In particular, it has been discovered that preventing or antagonizing a signaling pathway in a cell for a growth factor of the TGFβ. family can result in neuronal differentiation of that cell."

However, unlike their teachings to their peers skilled in the art (Hemmati-Brivanlou et al, supra), their patent disclosure erects a remarkable proposal: "The ability of follistatin to regulate neuronal differentiation not only during development of the nervous system but also presumably in the adult state . . . indicates that NAs can be reasonably expected to facilitate control of adult neurons with regard to maintenance, functional performance, and aging of normal cells." (U.S. Pat. No. 6,686,198; Col. 13, lines 35-10). Other than a "presumably" the patent offers no support whatsoever for this scientifically untenable proposal. As noted above, the only documentation presented relates to differentiation of embryonic Xenopus cells, which evidence those skilled in this art recognize as not probative of any effect on post-mitotic, terminally-differentiated cells like adult neurons.

SUMMARY OF THE INVENTION

One aspect of the invention is a method of promoting regeneration of a lesioned CNS axon of a mature neuron determined to be subject to regeneration inhibition by Smad2/3 mediated TGFbeta signaling. The method comprises the steps of: (a) contacting the neuron with an inhibitor of Smad2/3 signaling sufficient to promote regeneration of the axon; and (b) detecting a resultant regeneration of the axon. In preferred embodiments the inhibitor is selected from the group consisting of an activin inhibitor, an activin receptor-like kinase (ALK) inhibitor, and a Smad2/3 inhibitor.

Inhibitors that selectively inhibit an ALK include SB-431542, SB-505124, and GW788388. Other inhibitors include Smad7, and Smad2/3 siRNA.

In various embodiments, the lesion results from a traumatic injury, an acute spinal cord injury, or CNS degeneration. In a specific embodiment, the axon is a CNS axon of a sensory neuron, or a CNS axon of a cerebellar granule neuron.

The detecting step may be effected by an indirect or a direct assay of axon regeneration.

Another aspect of the invention is a CNS-implantable solid or semi-solid device comprising an inhibitor of Smad2/3 signaling, said device selected from a biodegradable matrix, fiber, pump, stent, and adsorbable gelatin.

DETAILED DESCRIPTION OF SPECIFIC EMBODIMENTS OF THE INVENTION

We have found that Smad2/3 signaling induced by TGFβ-family growth factors can reduce axon elongation ability in both embryonic and adult neurons through a canonical Smad signaling pathway. We show that inhibiting such signaling provides a novel therapeutic strategy for promoting regeneration of an axon of a mature neuron after neural injury. Our invention provides methods and compositions for promoting regeneration of a lesioned CNS axon of a mature neuron determined to be subject to regeneration inhibition by Smad2/3 signaling. The method comprises the steps of: contacting the neuron with an inhibitor of Smad2/3 signaling sufficient to promote regeneration of the axon; and detecting a resultant regeneration of the axon.

The lesioned sensory axon is subject to regeneration inhibition by Smad signaling. Smad signaling in a neuron can be detected by antibody specific for phosphorylated Smad2/3. In one example, the lesioned axon is a CNS axon of a dorsal root ganglion (DRG) sensory neuron, and the Smad2/3 signaling is activated due to the contact of the neuron's peripheral axon with TGFβ-family growth factors that are released from the target tissue and taken up by the neuron. In another example, the lesioned axon is a CNS axon of a cerebellar granule neuron. The mature (i.e. terminally-differentiated, non-embryonic) neuron may be in vitro or in situ in a patient. In specific embodiments, the patient is a mammal (e.g. human, companion animal, livestock animal, rodent or primate animal model for neurodegeneration or CNS injury, etc.).

The lesion can result from traumatic injury, stroke, pressure build-up, chronic neurodegeneration, etc. In a particular embodiment, the lesion results from acute or traumatic injury such as caused by contusion, laceration, acute spinal cord injury, etc. In certain embodiments, the contacting step is initiated within 96, 72, 48, 24, or 12 hours of formation of the lesion. The inhibitor can be administered to the injured neuron in combination with, or prior or subsequent to, other treatments such as the use of anti-inflammatory or anti-scarring agents. In a specific embodiment, the lesion results from acute spinal cord injury and the method additionally comprises contacting the neuron with methylprednisolone sufficient to reduce inflammation of the spinal cord. In another embodiment, the lesion results from neurodegeneration which, for example, can be caused by neurotoxicity or a neurological disease or disorder such as Huntington's disease, Parkinson's disease, Alzheimer's disease, multiple system atrophy (MSA), glaucoma, etc.

The inhibitor of Smad2/3 signaling may work by inhibiting binding of a ligand (e.g. activin and/or TGFβ) to an activin receptor-like kinase (ALK) that phosphorylates and activates Smad2/3, by inhibiting binding of Smad2/3 to activated ALK, by inhibiting expression of Smad2/3, by counteracting the activation of Smad 2/3, etc. In a specific embodiment the inhibitor is selected from the group consisting of an activin inhibitor, an ALK inhibitor, and a Smad2/3 inhibitor.

In a preferred embodiment, the inhibitor is an ALK inhibitor, which may function by inhibiting binding of a ligand to the ALK, by inhibiting the activity of ALK, or by competing with Smad2/3 for binding to activated ALK. In a specific embodiment, the inhibitor selectively inhibits ALK-4, -5, and/or -7 (i.e. it has less of an inhibitory effect on the other ALK family members). Examples of such selective inhibitors include 2-(5-benzo[1,3]dioxol-5-yl-2-tert-butyl-3H-imidazol-4-yl)-6-methylpyridine hydrochloride (SB-505124); 4-(5-benzo(1,3)dioxol-5-yl-4-pyridin-2-yl-1H-imidazol-2-yl)benzamide (SB-431542); and phenylpyridine pyrazoles such as 4-{4-[3-(Pyridin-2-yl)-1H-pyrazol-4-yl]pyridin-2-yl}-N-(tetrahydro-2H-pyran-4-yl)benzamide (GW788388). These and other small molecule inhibitors of ALK that can be used in the invention are well-known (see e.g. Byfield et al, Mol Pharmacol (2004) 65:744-752; Callahan et al, J Med Chem. (2002) 45:999-1001; Gellibert et al, J Med Chem. (2006) 49:2210-21; Hjelmeland, 2004).

In another embodiment the inhibitor is Smad7, which inhibits Smad2/3 signaling by competing with Smad2/3 for binding to an activated ALK. The Smad7 can be contacted with the neuron by causing Smad7 up regulation in the neuron, such as by introducing a Smad7 expression construct into the neuron (see Example 1).

In other embodiments, the inhibitor directly inhibits Smad2/3 by binding to it (e.g. an anti Smad2/3 antibody) or by inhibiting Smad2/3 expression (e.g. a Smad2/3 siRNA).

The inhibitor is contacted with the neuron using any suitable drug delivery method and treatment protocol that is sufficient to promote regeneration of the axon. For in vitro methods, the inhibitor is added to the culture medium, usually at nanomolar or micromolar concentrations. For in situ applications, the inhibitor can be administered orally, by intravenous (i.v.) bolus, by i.v. infusion, intracranially, intraperitoneally, intraventricularly, intrathecally, by epidural, etc. In a specific embodiment, the inhibitor is contacted with the neuron using an implantable device that contains the inhibitor and that is specifically adapted for delivery to a CNS axon of neuron. Examples of devices include solid or semi-solid devices such as controlled release biodegradable matrices, fibers, pumps, stents, adsorbable gelatin (e.g. Gelfoam), etc. The device may be loaded with premeasured, discrete and contained amounts of the inhibitor sufficient to promote regeneration of the axon. In a particular embodiment, the device provides continuous contact of the neuron with the inhibitor at nanomolar or micromolar concentrations, preferably for at least 2, 5, or 10 days.

The subject methods further comprise the step of detecting a resultant regeneration of the axon. For in vitro applications, axonal regeneration can be detected by any routinely used method to assay axon regeneration such as a neurite outgrowth assay. For in situ applications, axonal regeneration can be detected directly using imaging methodologies such as MRI. More commonly, axonal regeneration will be detected indirectly or inferentially by neurological examination showing improvement in the patient's neural function. The detecting step may occur at any time point after initiation of the treatment, e.g. at least one day, one week, one month, three months, six months, etc. after initiation of treatment. In certain embodiments, the detecting step will comprise an initial neurological examination and a subsequent neurological examination conducted at least one day, week, or month after the initial exam. Improved neurological function at the subsequent exam compared to the initial exam indicates resultant axonal regeneration. The specific detection and/or examination methods used will usually be based on the prevailing standard of medical care for the particular type of axonal lesion being evaluated (i.e. trauma, neurodegeneration, etc.).

The invention also provides inhibitor-eluting or inhibitor-impregnated CNS-implantable solid or semi-solid devices. Examples of CNS implantable devices include polymeric microspheres (e.g. see Benny et al., Clin Cancer Res. (2005) 11:768-76) or wafers (e.g. see Tan et al., J Pharm Sci. (2003) 4:773-89), biosynthetic implants used in tissue regeneration after spinal cord injury (reviewed by Novikova et al., Curr Opin Neurol. (2003) 6:711-5), biodegradable matrices (see e.g. Dumens et al., Neuroscience (2004) 125:591-604), bio-degradable fibers (see e.g. U.S. Pat. No. 6,596,296), osmotic pumps, stents, adsorbable gelatins (see e.g. Doudet et al., Exp Neurol. (2004) 189:361-8), etc. Preferred devices are particularly tailored, adapted, designed or designated for CNS implantation. The implantable device may contain one or more additional agents used to promote or facilitate neural regeneration. For example, in one embodiment, an implantable device used for treatment of acute spinal cord injury contains the inhibitor and methylprednisolone or other anti-inflammatory agents. In another embodiment, the implantable device contains the inhibitor and a nerve growth factor or hormone that promotes neural cell survival, growth, and/or differentiation, such as brain-derived neurotrophic factor (BDNF), ciliary neurotrophic factor (CNTF), nerve growth factor (NGF), etc.

EXAMPLE 1

Inhibitors of Smad2/3 Signaling Promotes Axonal Growth in Adult DRG and Postnatal Cerebellar Granule Neurons Our prior experiments demonstrated that activin A triggers a decline in axonal growth ability in embryonic DRG neurons and reduces axonal elongation ability in adult DRG neurons. This example shows that inhibiting the Smad2/3 signaling pathway enhances the intrinsic growth state of adult DRG neurons. It is known that Smad7 can bind to activated TGFβ receptor family members in competition with receptor-Smads including Smad2 and Smad3, and thus inhibit the downstream signaling pathways (Hayashi et al., 1997; Nakao et al., 1997).

For overexpression of Smad7 in DRGs, adult rat DRG neurons were co-transfected by electroporation with 2 μg pEGFP (Invitrogen) and 5 μg of an expression construct for FLAG-tagged Smad7 (Nakao et al., 1997) or control plasmid using the Rat Neuron Nucleofector Kit (Amaxa) following manufacturer's protocol. After brief purification, the neurons were plated at a density of 200-500 cells/mm2. For overexpression of Smad7 in cerebellar granule neurons (CGN), CGNs from P6 Sprague-Dawley rat pups were dissected, plated onto poly-D-lysine (20 μg/ml), and cultured in Basal Medium Eagle (Gibco) supplemented with 10% calf serum, 25 mM KCl, 2 mM L-glutamine, penicillin and streptomycin, at a density of 2.5×103 cells/mm2. CGNs were co-transfected with pEGFP and Smad7 or control plasmid at a 1 to 3 ratio using a modified calcium phosphate transfection method as described before (Konishi et al., 2004). After culturing, neurons were fixed with 4% paraformaldehyde and axons were visualized by immunostaining with a neuronal-specific anti-βIII-tubulin antibody (Tuj 1, Covance) for dissociated cultures or anti-neurofilament antibody for explant cultures. Expression of CGRP was visualized by immunostaining with rabbit anti-CGRP antibody (Sigma). For transfected neurons, axons were co-immunostained with an anti-GFP antibody (Abcam) and an anti-FLAG antibody (Sigma).

Average axon length of the longest neurite from every individual neuron was measured and quantified as described before (Koprivica et al., 2005; Wang et al., 2002a; Wang et al., 2002b). Branching frequency was measured by dividing the number of branches from the longest neurite by the length of the neurite, as previously described (Smith and Skene, 1997). All measurements were made from at least 150 neurons per condition, from duplicate wells and from three independent experiments.

Overexpression of Smad7, but not control GFP, in dissociated adult rat DRG neurons significantly enhanced the rate of axonal growth. This increased axonal growth ability is not limited to DRG neurons, as Smad7 expression could also dramatically increase axonal growth rate in cerebellar granule neurons (CGNs) from postnatal rats. This promoting effect became stronger with time.

We next examined whether inhibiting this signaling pathway could enhance the intrinsic growth state of adult DRG neurons by pharmacological approaches. We injected SB505124 or the same volume of saline into the adult DRG (L4 and L5). 3 or 7 days post-injection, the axonal growth ability of injected DRG neurons were assayed by culturing DRG neurons in vitro for 12 hrs. In our pilot experiments, we tested different concentrations of SB505124 for injection in the range of 1-100 mM and found that 2 µl of 5-10 mM SB505124 resulted in significant reduction of phospho-Smad2 in the injected DRGs. SB505124, but not the same volume of saline control, significantly increased axonal elongation and reduced branching frequency of DRG neurons.

EXAMPLE 2

Inhibition of Smad2/3 Signaling Promotes Axonal Regeneration after Spinal Injury in Rats This animal study demonstrates that in an animal model for spinal injury, axonal regeneration can be promoted by intrathecal catheter administration of siRNA against Smad2/3, or by tail vein injection of an inhibitor of TGF-β1 activin receptor-like kinases. Methodology for this animal study was adapted from Nash et al (J. Neurosci, 2002 22:7111-7120) and Luo et al (Molecular Pain, 2005 Sep. 28;1:29).

Adult Sprague Dawley rats (300-400 gm) are trained and tested in a directed forepaw reaching (DFR) apparatus which measures grasping ability. The apparatus, which is described in detail by Nash et al., supra, is a box that consists of two compartments: a main compartment for housing the rats and a minor compartment for the food, separated by a Plexiglas divider. The minor compartment is subdivided into slots of equal size, each holding a pellet of food. Between the slots and the Plexiglas there is a gap. The apparatus is configured such that in order to retrieve a food pellet from a slot, a rat must extend a forelimb through a hole in the Plexiglas divider, and grasp the pellet and lift it over the gap and out of the slot. If the rat merely rakes the food in the slot towards the hole in the Plexiglas, the food will drop from the slot into the gap and fall to the floor of the minor compartment. The floor of the minor compartment can be configured to allow a rat to retrieve food that drops or it can be lowered to prevent the rat from reaching dropped food. Prior to inducing spinal injury, the rats are food restricted, receiving ~3 gm food/100 gm body weight per day, before and throughout training and testing. Weight is monitored to ensure that rats are reduced to no less than 80% of their original body weight at any time. All rats are given shaping periods for 2-3 d in the box to allow them to learn the task while they become familiar with the testing situation. Animals are trained twice per day for 5 d and then tested twice per day for 5 d, and presurgical DFR data is collected. During the testing period, rats are given 5 min to complete the task and are allowed to make as many attempts as they want during this time period. Rats are required to return to at least 95% of their original weight to ensure that they are healthy before undergoing surgery.

Rats are randomly assigned to control or experimental groups. Sham control rats undergo surgical procedure without lesioning, and with or without placement of an intrathecal catheter. Lesioned control rats receive no treatment, tail injection vehicle only treatment, intrathecal catheter only treatment, intrathecal catheter with vehicle only treatment, or intrathecal catheter and mismatch siRNA treatment. After anesthesia with isoflurane, the rats are placed on an operating board in such a way as to bend the cervical spinal cord for maximum exposure. A laminectomy is performed exposing the dorsum of the spinal cord between C2 and C4. The dorsal columns are identified bilaterally, and, in all rats except for those in the sham group, a suture needle is passed through the spinal cord, isolating the dorsal funiculus. The suture thread is gently lifted, and a pair of iridectomy scissors is used to bilaterally transect the dorsal funiculus, thereby transecting the dorsal corticospinal tract (CST). Visualization of the dorsal horns and the central gray commissure confirms accuracy of the lesion borders. A pledget of biodegradable Gelfoam soaked in a fluorescent retrograde tracer, Fluorogold (3% in 0.9% saline; Molecular Probes), is placed in the lesion site to identify the neurons whose axons are transected, confirming the lesion. Rats designated for siRNA treatment or corresponding control treatment are implanted with intrathecal catheters adjacent to the lesion site. The overlying muscles and skin are sutured, and the rats are placed on a heating pad to maintain body temperature. Each rat receives a single dose of buprenorphine (0.1 mg/kg) immediately after surgery to alleviate pain.

One hour after the spinal cord is lesioned, the rats in the SB-505124 group receive a bolus injection of SB-505124 (30 mg/kg) in 0.9% saline administered via a tail vein. The treatment is repeated every 24 hours on days 1 through 7 post-lesion. Vehicle only control rats undergo the same treatment but are injected with an equal volume of 0.09% saline in a tail vein. At the same treatment time points as the SB-505124 group, the Smad2/3 siRNA group and corresponding controls receive 10 µl rat Smad2/3 siRNA (Dharmacon, Lafayette, Colo.), mismatch siRNA, or transfection reagent only delivered to the spinal cord via the catheters. The siRNA (or mismatch siRNA control) complexes are prepared immediately prior to administration by mixing the RNA solution (200 µM in annealing buffer) with a transfection reagent, i-Fect™ (Neuromics, Edina, Minn.), in a ratio of 1:4 (w:v). At this ratio, the final concentration of RNA as an RNA/lipid complex is 2 µg in 10 µl.

Rats are trained twice per week during weeks 2-5 after surgery. Some rats may be profoundly impaired such that they may not be able to grasp food in the DFR task in the early postsurgical period. In this case, the apparatus can be configured to allow the rats to rake food into the main compartment that drops from the slot onto the floor of the minor compartment (see Nash et al., supra). This ensures that the reaching portion of the DFR task does not extinguish. The severity of the grasping impairment decreases as the postsurgical period increases, and the configuration of the apparatus that does not permit food raking can be gradually reestablished. By the end of the postsurgical recovery period, all rats are able to successfully perform the DFR task, to some degree. During the sixth week after surgery, rats are tested twice per day for 5 d, and postsurgical DFR data is collected by a blinded investigator. Just as during the presurgery testing period, the rats are allowed 5 min to complete the task during the postsurgery testing period and are allowed to make as many attempts as they want during this time period. The data is collected in terms of total number of attempts and percentage of successful attempts. An attempt is scored only when a rat reaches into a slot and displaces the pellet or drops it to the floor of the minor compartment. A successful attempt is scored when a rat grasps a pellet, lifts it over the gap and pulls it through the Plexiglas divider into the main portion of the testing apparatus.

Sham animals perform the DFR task as well postsurgically as they do presurgically, demonstrating that only the lesion, and no other portion of the surgical procedure, inhibits the rats' abilities to perform the DFR task. The lesion and vehicle groups are the most impaired of all of the groups after surgery. The lesion and vehicle groups are able to perform the DFR task with a success rate of only about 40%. Significantly better performance by the SB505124- and Smad2/3 siRNA-treated groups demonstrates the effect of the treatment on functional recovery after spinal injury.

Seven weeks after injury, rats are prepared for injection of biotin dextran tetramethylrhodamine (BDT; Molecular Probes). This fluorescent anterograde tracer, injected into the primary motor cortex, is used to label CST axons caudal to the lesion site in the spinal cord. After anesthesia with isoflurane (5%), rats are placed in a stereotaxic instrument, and a total of six stereotaxically determined holes (0.9 mm diameter) are drilled in the skull over the primary motor cortices associated with the forelimbs. The anteroposterior (AP) and mediolateral (ML) coordinates for these injections, from bregma, are as follows: ±0.5 AP and ±3.5 ML; ±1.5 A/P and ±2.5 ML; and ±2.5 AP and ±1.5 ML. All injections are delivered at a depth of 2.5 mm from the surface of the skull. A 10 µl Hamilton syringe is used to inject BDT bilaterally into layer V of the cortex. Three injections into each cortical hemisphere are used to administer a total of 1.2 µl of the anterograde tracer. Bone wax (Ethicon, Somerville, N.J.) is used to seal the holes in the skull, the scalp is sutured, and a single dose of buprenorphine (0.1 mg/kg) is administered immediately after surgery to alleviate pain. Rats are killed 3 d after tracer injections.

Seven weeks and 3 d after lesioning, rats are anesthetized with chloral hydrate (10 ml/kg) and perfused transcardially with 300 ml of PBS, pH 7.4, followed by 300 ml of 4% paraformaldehyde in 0.1 M phosphate buffer. After the animals are killed, all brains and spinal cords are removed and soaked overnight in 30% sucrose in a 0.1M phosphate buffer solution. The brains are cut coronally and the spinal cords are cut horizontally at a thickness of 20 µm with a freezing microtome and mounted on ProbeOn (Fisher Scientific, Pittsburgh, Pa.) coated slides. Brain and spinal cord sections are examined using a Nikon (Tokyo, Japan) Labophot fluorescent microscope, and images are captured using a digital still camera. The forelimb representation of the primary motor cortex is identified based on the stereotaxic BDT injection sites. The primary motor cortex is examined in all rats. Presence of Fluorogold-labeled neurons in layer V of the primary motor cortex, confirms that the dorsal CST axons were transected during the lesioning procedure. Because all CST axons located in the dorsal funiculus are transected during surgery and not just those in the forelimb representation, Fluorogold-labeled neurons are found throughout the primary motor cortex in layer V. The only exception to this labeling pattern is in the brains of the rats in the sham group whose brains have no Fluorogold label.

The spinal cord caudal to the lesion is examined, and the BDT-labeled axons occupying the region of the spinal cord normally occupied by the dorsal CST are counted. For each section, the number of BDT-labeled axons is counted at 3 mm intervals caudal to the lesion, beginning 1 mm distal to the injury (i.e., 1 mm, 4 mm, 7 mm, etc.) and ending 19 mm caudal to the lesion site. Innervation of the rat forepaw extends to T1, a distance of 15.1 mm from the lesion at C3. Therefore, analysis of the axons out to 19 mm caudal to the lesion ensures that the entire distance representing the forepaw is examined. At each interval, the total number of BDT-labeled axons (left and right CST combined) along a 500 µm length (length of microscope field) is counted. In each field counted, the focal plane is adjusted up and down to ensure that a single continuous axon is not double counted if it traverses out of the focal plane and reemerges farther down in the same field. The number of BDT-labeled axons present is examined for control and experimental groups at each of the distances (i.e. 1, 4, 7 . . . and 19 mm caudal to the lesion site). Throughout all of the examined intervals, the mean number of axons is highest in the sham group, and, at each distance examined, the mean number of labeled axons in the sham group is significantly higher than in all other groups. No significant difference is observed between the means of the lesion, vehicle, and mismatch siRNA groups at any distance examined. In these groups, axons are found only a short distance caudal to the injury, and, by 10 mm distal to the lesion to the farthest distance examined, all of the tissue is virtually devoid of axons. Significantly more labeled axons at each distance in the SB-505124- and Smad2/3 siRNA-treated group compared to lesioned control rats demonstrates that these treatments promote axonal regeneration after spinal injury.

EXAMPLE 3

Effect of ALK Inhibition after Cortical Impact Injury in Rats

We adapted methodology from Cherian et al. (J Pharmacol Exp Ther. (2003) 304:617-23), to test the effects of different doses and treatment schedules of SB-431542 on a rat model of brain impact injury. A total of 60 male Evans rats weighing 300 to 400 g are assigned to one of the following doses injected intraperitoneally (i.p.): none (saline control group), 1, 10, and 50 mg/kg/day SB-431542. The rats are further assigned to a treatment duration of 1, 3, 7, or 14 days, with 4 rats in each treatment group, and 3 rats in each control group (i.e. saline administered for 1, 3, 7, or 14 days). The details of the methods to produce the impact injury have been previously described (Cherian et al., J. Neurotrauma (1996) 13:371-383). Briefly, the head of the rat is fixed in a stereotaxic frame by ear bars and incisor bar. A 10-mm diameter craniotomy is performed on the right side of the skull over the parietal cortex. An impactor tip having a diameter of 8 mm is centered in the craniotomy site perpendicular to the exposed surface of the brain at an angle of approximately 45 degrees to the vertical. The tip is lowered until it just touches the dural surface. The impactor rod is then retracted, and the tip advanced an additional 3 mm to produce a brain deformation of 3 mm during the impact. Gas pressure applied to the impactor is adjusted to 150 psi, giving an impact velocity of approximately 5 m/s and duration of approximately 150 to 160 ms.

Rats are fasted overnight and anesthetized with 3.5% isoflurane in 100% oxygen in a vented anesthesia chamber. Following endotracheal intubation with a 16-gauge Teflon catheter, the rats are mechanically ventilated with 2% isoflurane in 100% oxygen for the surgical preparation and for the impact injury. Intracranial pressure (ICP) is monitored by a 3F microsensor transducer (Codman & Schurtleff, Randolph, Mass.) inserted in the left frontal lobe, well away from the impact site. ICP is monitored during the impact injury as a measure of the severity of the injury. Rectal temperature is maintained at 36.5-37.5° C. by a heating pad, which is controlled by rectal thermistor. Brain temperature is kept constant at 37° C. with the help of a heating lamp directed at the head. Each dose of SB-431542 is dissolved in 1 ml of sterile 0.9% saline so that the volume delivered is the same for each group and only the dosage of SB-431542 varies. The first dose is administered within 1 hour following impact injury. After removing all catheters and suturing the surgical wounds, the rats are allowed to awaken from anesthesia. For the first 3 days post injury, the rats are treated with butorphanol tartrate, 0.05 mg of i.m. every 12 h (twice a day), for analgesia and enrofloxacin 2.27%, 0.1 ml of IM qd, to reduce the risk of postoperative infections. SB-431542 is administered once daily for the assigned treatment duration.

The outcome measures are performed by investigators who are blinded to the treatment group. At 2 weeks after the impact, the animals are deeply anesthetized with a combination of ketamine/xylazine/acepromazine and perfused transcardially with 0.9% saline, followed by 10% phosphate buffered formaldehyde. The entire brain is removed and fixed in 4% formalin. The fixed brains are examined grossly for the presence of contusion, hematoma, and herniation. The brains are photographed, sectioned at 2-mm intervals, and then embedded in paraffin. Hematoxylin and eosin (H&E) stained 9-µm thick sections are prepared for histologic examination. Particular care is made to include the largest cross-sectional area of cortical injury on the cut surface of the embedded sections. The H&E-stained coronal sections are digitized using a Polaroid Sprint Scanner (Polaroid Corporation, Waltham, Mass.) equipped with a PathScan Enabler (Meyer Instruments, Houston, Tex.). The injury volume is measured by determining the cross-sectional area of injury in each H&E-stained coronal image and multiplying by the thickness of the tissue between the slices. This slab volume technique is implemented on the image processing program Optimas 5.2 (Optimas Corporation, Seattle, Wash.). Neurons in the middle 1-mm segments of the CA1 and CA3 regions of the hippocampus are counted at a magnification of 200×. Neurons are identified by nuclear and cytoplasmic morphology, and individual cells are counted whether normal or damaged. Neurons with cytoplasmic shrinkage, basophilia, or eosinophilia or with loss of nuclear detail are regarded as damaged. The regions measured are 1 mm long and 1 mm wide (0.5 mm on either side of the long axis of the segment). The total number of neurons and the number of neurons that appear normal are expressed as neurons per squared millimeter.

EXAMPLE 4

Improved Neurological Outcome Following SB-505124 Treatment for Acute Spinal Cord Injury We adapted our protocol for this study from the Sygen® Multicenter Acute Spinal Cord Injury Study described by Geisler et al (Spine (2001) 26:587-598). It is a prospective, double-blind, randomized, stratified, multicenter trial, randomizing approximately 800 patients so as to have at least 720 completed and evaluable in each of three initial treatment groups: placebo, low-dose SB-505124, and high-dose SB-505124. The patients are stratified into six groups, according to three degrees of injury severity (American Spinal Injury Association grades A, B, and C+D) and two levels of anatomic injury (cervical and thoracic). The trial is sequential with preplanned interim analyses as each group of 720/4=180 patients reach their 26-week examination and become evaluable. Patients are required to have at least one lower extremity with a substantial motor deficit. Patients with spinal cord transection or penetration are excluded, as are patients with a significant cauda equina, brachial or lumbosacral plexus, or peripheral nerve injury. Gunshot injuries that do not penetrate the cord are allowed. Multiple trauma is allowed as long as it is not so severe as to prevent neurologic measurement evaluation or interpretation.

All patients are to receive the second National Acute Spinal Cord Injury Studies (NASCIS II) dose regimen of methylprednisolone (MPSS) starting within 8 hours after the spinal cord injury (SCI). To avoid any possible untoward interaction between MPSS and SB-505124 the study medication is not started until after completion of MPSS administration.

The placebo group has a loading dose of placebo and then 56 days of placebo. The low dose SB-505124 group has a 300-mg loading dose administered intravenously (i.v.) followed by 100 mg/day i.v. for 56 days. The high dose SB-505124 group has a 600-mg loading dose followed by 200 mg/day for 56 days.

The baseline neurologic assessment includes both the AIS and detailed American Spinal Injury Association (ASIA) motor and sensory examinations. Modified Benzel Classification and the ASIA motor and sensory examinations are performed at 4, 8, 16, 26, and 52 weeks after injury. The Modified Benzel Classification is used for post-baseline measurement because it rates walking ability and, in effect, subdivides the broad D category of the AIS. Because most patients have an unstable spinal fracture at baseline, it is not possible to assess walking ability at that time; hence the use of different baseline and follow-up scales. Marked recovery is defined as at least a two-grade equivalent improvement in the Modified Benzel Classification from the baseline AIS. The primary efficacy assessment is the proportion of patients with marked recovery at week 26. The secondary efficacy assessments include the time course of marked recovery and other established measures of spinal cord function (the ASIA motor and sensory scores, relative and absolute sensory levels of impairment, and assessments of bladder and bowel function).

The foregoing examples and detailed description are offered by way of illustration and not by way of limitation. All publications and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims

REFERENCES

Aguayo, et al. (1990). J Exp Biol 153, 199-224.

Ai, X., et al (1999). Mol Cell Neurosci 14, 506-518.

Attisano, L., and Wrana, J. L. (2002). Science 296, 1646-1647.

Basi, G. S., et al (1987). Cell 49, 785-791.

Bibel, M., and Barde, Y. A. (2000). Genes Dev 14, 2919-2937.

Bomze, H. M., et al (2001). Nat Neurosci 4, 38-43.

Campenot, R. B., and MacInnis, B. L. (2004). J Neurobiol 58, 217-229.

Caroni, P., and Becker, M. (1992). J Neurosci 12, 3849-3861.
Case, L. C., and Tessier-Lavigne, M. (2005). Curr Biol 15, R749-753.
Chong, M. S., et al (1996). J Comp Neurol 370, 97-104.
Chu, D. T., and Klymkowsky, M. W. (1989). Dev Biol 136, 104-117.
Derynck, R., and Zhang, Y. E. (2003). Nature 425, 577-584.
Filbin, M. T. (2003). Nat Rev Neurosci 4, 703-713.
Fitzgerald, M. (1991). J Physiol 432, 473-482.
Gibson, S. J., et al (1984). J Neurosci 4, 3101-3111.
Ginty, D. D., and Segal, R. A. (2002). Curr Opin Neurobiol 12, 268-274.
Goldberg, J. L., et al (2002). Neuron 33, 689-702.
Hall, A. K., et al (1997). J Neurosci 17, 2775-2784.
Hall, A. K., et al (2001). Dev Biol 229, 263-270.
Hall, Z. W., and Sanes, J. R. (1993). Cell 72 Suppl, 99-121.
Hayashi, H., et al (1997). Cell 89, 1165-1173.
Harel and Strittmatter (2006) Nat Rev Neurosci. 7(8):603-16
Hippenmeyer, S., et al (2004). Trends Neurosci 27, 482-488.
Hjelmeland, M. D., et al (2004). Mol Cancer Ther 3, 737-745.
Hoffman, P. N. (1989). J Neurosci 9, 893-897.
Howe, C. L., and Mobley, W. C. (2005). Curr Opin Neurobiol 15, 40-48.
Konishi, Y., et al (2004). Science 303, 1026-1030.
Koprivica, V., et al (2005). Science 310, 106-110.
Lankford, K. L., et al (1998). J Comp Neurol 391, 11-29.
Lee, Y., et al (1985a). Brain Res 330, 194-196.
Lee, Y., et al (1985b). Neuroscience 15, 1227-1237.
Liu, R. Y., and Snider, W. D. (2001). J Neurosci 21, RC164.
Maness, P. F., et al (1988). Proc Natl Acad Sci USA 85, 5001-5005.
Massague, J., et al (2005). Genes Dev 19, 2783-2810.
McMahon, S. B., et al (1989). Neuroscience 33, 67-73.
Miller, F. D., et al. (1989). J Neurosci 9, 1452-1463.
Nakao, A., et al (1997). Nature 389, 631-635.
Neumann, S., et al (2005). Proc Natl Acad Sci USA 102, 16848-16852.
Neumann, S., and Woolf, C. J. (1999). Neuron 23, 83-91.
Oudega, et al (1994). Exp Neurol 129, 194-206.
Richardson, P. M., and Issa, V. M. (1984). Nature 309, 791-793.
Richardson, P. M., and Verge, V. M. (1986). J Neurocytol 15, 585-594.
Rogister, et al. (1993). J Neurosci Res 34, 32-43.
Saito, K. (1979). J Physiol 294, 581-594.
Schwab, M. E., and Bartholdi, D. (1996). Physiol Rev 76, 319-370.
Shi, Y., and Massague, J. (2003). Cell 113, 685-700.
Silver, J., and Miller, J. H. (2004). Nat Rev Neurosci 5, 146-156.
Skene, J. H., et al (1986). Science 233, 783-786.
Smith, D. S., and Skene, J. H. (1997). J Neurosci 17, 646-658.
Stark, B., et al (2001). Brain Res. 913, 47-56.
Thuret et al (2006) Nat Rev Neurosci. 2006 August; 7(8): 628-43.
Wang, K. C., et al (2002a). Nature 420, 74-78.
Wang, K. C., et al (2002a). Nature 417, 941-944.
Yiu and He (2006) Nat Rev Neurosci. 2006 7(8):617-27.
Zweifel, L. S., et al (2005). Nat Rev Neurosci 6, 615-625.

What is claimed is:

1. A method of promoting neurite outgrowth, the method comprising the steps of:
(a) contacting a neuron in situ with an inhibitor of Smad2/3 signaling;
(b) isolating and culturing the neuron; and
(c) detecting a resultant promotion of neurite outgrowth of the neuron in vitro, wherein the neuron is an adult dorsal root ganglion (DRG) cell and the inhibitor is 2-(5-benzo[1,3]dioxol-5-yl-2-tert-butyl-3H-imidazol-4-yl)-6-methylpyridine hydrochloride (SB-505124).

* * * * *